United States Patent [19]

Pozzo

[11] Patent Number: 5,069,877

[45] Date of Patent: Dec. 3, 1991

[54] ARTICLE FOR DIFFUSING VOLATILE SUBSTANCES, AND IN PARTICULAR PERFUME

[75] Inventor: Michel L. Pozzo, Neuilly Sur Seine, France

[73] Assignee: Ateliers De Conceptions Et D'Innovations Industrielles, Courbevoie, France

[21] Appl. No.: 320,068

[22] Filed: Mar. 7, 1989

[30] Foreign Application Priority Data

Mar. 8, 1988 [FR] France .................. 88 02924

[51] Int. Cl.⁵ ............................. A61L 9/02
[52] U.S. Cl. ......................... 422/4; 422/5; 422/120; 422/121; 422/122; 422/123; 422/125; 422/306; 239/35; 239/54; 239/57; 239/60
[58] Field of Search ............. 422/4, 5, 120–123, 422/125, 306; 239/35, 54, 57, 60

[56] References Cited

U.S. PATENT DOCUMENTS

| | | | |
|---|---|---|---|
| 2,220,583 | 11/1940 | Schnebly et al. | 422/305 X |
| 4,184,099 | 1/1980 | Lindauer et al. | 313/315 |
| 4,367,203 | 1/1983 | Landsberger | 422/5 X |
| 4,493,011 | 1/1985 | Spector | 422/5 X |

FOREIGN PATENT DOCUMENTS 0110678  6/1984  European Pat. Off.

Primary Examiner—Robert J. Warden
Assistant Examiner—Lynn M. Kummert
Attorney, Agent, or Firm—Blakely Sokoloff Taylor & Zafman

[57] ABSTRACT

A consumable article for diffusing active volatile substances, in particular perfume, into the ambient atmosphere, the article comprising a support element of shrinkable material, in particular heat shrink material, with the volatile substance being absorbed in the support element. The invention also provides a method of diffusing volatile substances, in particular perfume, by means of an article of this type, and also a device for implementing the method.

12 Claims, 1 Drawing Sheet

U.S. Patent  Dec. 3, 1991  5,069,877
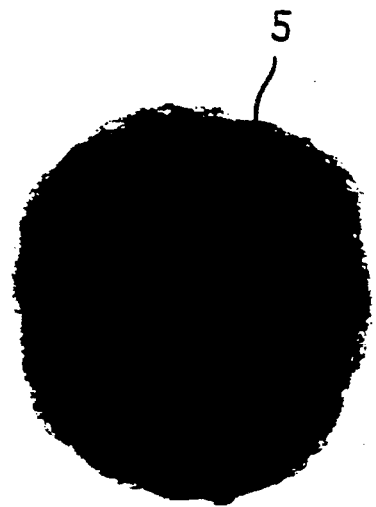
FIG_1
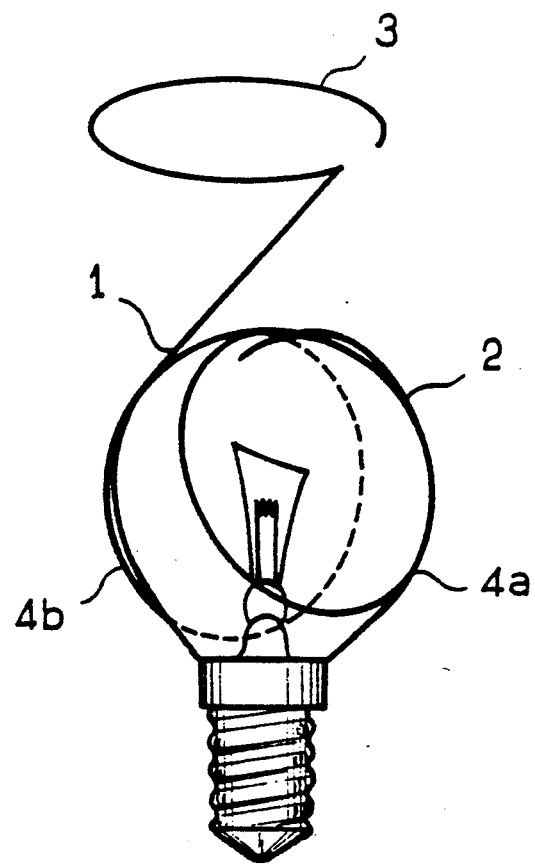
FIG_2

ARTICLE FOR DIFFUSING VOLATILE SUBSTANCES, AND IN PARTICULAR PERFUME

The present invention relates to a consumable article for diffusing active volatile substances, in particular perfume, into the ambient atmosphere. The invention also relates to a method of diffusing said substances and to a device for supporting said article and suitable for use in the diffusion method.

In the present application, the term "active volatile substances" is used to designate, in particular, deodorants, insecticides, bactericides, substances for repelling or attracting animals, and above all perfumes.

BACKGROUND OF THE INVENTION

Numerous techniques are used for diffusing perfumes in the atmosphere. One of the simplest techniques makes use of diffusion devices comprising liquid perfume contained in a receptacle such as a small cup placed in the vicinity of a source of heat, which may be constituted, in particular, by an electric lightbulb when switched on. This type of device naturally suffers from certain dangers in use since it requires an inflammable liquid to be handled in contact with a relatively strong source of heat, supposing an electric lightbulb is being used, for example.

In order to avoid this type of manipulation, proposals have been made to use support elements such as porous granules made of plastic material or pellets of cellulose in which the substances to be diffused are absorbed. However, such elements are generally relatively expensive for the use to which they are put, and in addition they do not always provide satisfactory diffusion of the absorbed substance. Finally, such elements are not consumable and in particular, they do not make it possible to keep track of, and more precisely to observe, the degree to which the element has been used up, i.e. for the purpose of refilling it or preferably changing it in timely manner.

It is preferable for users not to refill supports of this type and for such supports to be consumable, or at least for them to need changing when the substance absorbed therein has been diffused. It is well known that conflicting mixtures of perfumes can have highly disagreeable effects on the resulting odor due to various incompatibilities between different perfumes. Errors of this type may therefore take place if a support element is refilled using a perfume which is different from the preceding perfume and assuming that traces of the preceding perfume are still present.

In this context, it should be observed that in devices using a liquid perfume contained in a receptacle in contact with a source of heat, it is necessary for the receptacle to be cleaned carefully between each period of use whenever the perfume substance is changed.

An aim of the present invention is thus to provide a diffusion article which ensures good diffusion of the active volatile substance to be diffused while mitigating the above-mentioned drawbacks of the prior art.

SUMMARY OF THE INVENTION

To do this, the present invention provides a consumable article for diffusing active volatile substances, in particular perfume, into the ambient atmosphere, the article comprising a support element of shrinkable material, in particular heat shrink material, said substance being absorbed in said element.

According to the invention, said substance which impregnates said element is "sweated out" as it were as the element shrinks until it has shrunk completely. This type of diffusion of the impregnating substance is particularly effective since it results not only from the physio-chemical evaporation conditions of the substance related to temperature, where applicable, but also from mechanical stresses due to the support element shrinking. The material may be heat-shrink material, in which case it shrinks by virtue of temperature being applied thereto. However, the invention may make use of a material which shrinks at ambient temperature merely on coming into contact with ambient air, in which case it is not essential for it to be in the proximity of a heat source in order to obtain diffusion. It may also be noted that such shrinking makes it possible to track and observe the rate at which the diffusion article is progressively used up.

In a particularly appropriate embodiment of the invention, said support element is constituted by heat shrink textile fibers, which are preferably not woven, but are bonded by a polymer resin. It may be in the form of a pellet or a washer. This type of material is good for retaining the substance in the support element and behaves somewhat like a sponge. The article can thus be used without any risk of losing liquid, and thus without risk of accident, given the necessary proximity to a source of heat in order to cause said substance to be diffused. The absorption of the substance in the support element disengages the fibers from the binder and facilitates fiber shrinkage.

Thus, one particular type of support constituted by non-woven chloro-fibers bonded by a polyvinyl chloride resin shrinks from 120° C. when not dampened, but from as little as 60° C. to 80° C. when dampened by being filled with a solution comprising a perfume substance.

Advantageously, said substance is diluted in a solvent which is little or not volatile when the temperature is less than the shrinking temperature of the support element impregnated with said substance. For example, the substance may be diluted in an oily type of solvent such as a glycol type solvent, and in particular dipropylene glycol or ethylene diglycol.

Diluting the substance in a solvent not only makes it possible to thoroughly impregnate the support element and thus facilitate shrinkage thereof, but also serves to homogenize the distribution of said substance throughout the support element, thereby obtaining regular diffusion of said substance into the ambient atmosphere over time. Using a non-volatile solvent offers the advantage of making it possible to store the article prior to use in a state of dampness which favors good shrinking.

However, in order to ensure that the article is stored under the best possible conditions, it is preferable for it to be packed in a pocket in a box which is airtight and lightproof, for example a polypropylene-lined aluminum box. It is preferable to avoid exposing perfume to light in order to prevent chemical degradation thereof.

The present invention also provides a method of diffusing a volatile substance, in particular perfume the method comprising: absorbing said substance in a support element of shrinkable material, in particular of heat shrink material, and diffusing said substance into the atmosphere by causing said support element to shrink.

In a preferred implementation of the method, the support element shrinks on being heated, thereby also causing said substance to be evaporated and thus diffusing it.

The present invention thus provides a diffusion method using an article as specified above, in particular placing said article in the proximity of a heat source.

The invention also provides a support device for an article in accordance with the invention and suitable for implementing the method of diffusing a volatile substance, and in particular a perfume, wherein the device essentially comprises a pad type element constituted by intermeshed wires of metal, which are then compressed in order to give a pad type element having a shape suitable for receiving said article.

This device may be placed in the proximity of a heat source, in particular an electric lightbulb, by using appropriate fixing means, e.g. directly to the lightbulb by means of a metal wire with one end fixed to the device and with its other end in the form of a two-loop spring, with the bulb being inserted between the two loops of the spring.

The structure of this device imparts highly advantageous technical effects thereto. Firstly, it dissuades the user from directly inserting a liquid therein in a dangerous manner, as may happen when the article is supported by a cup. Secondly, and above all, this device makes it possible to mitigate a series of drawbacks encountered when the article in accordance with the invention is supported by a cup in the proximity of a bulb, for example.

It has been observed that when the article is placed in a cup, it shrinks too much and too quickly due to the temperature rising too far at certain points on the cup, in particular points closest to the bulb. Liquid is expelled from the article in such quantities that it does not all evaporate as it is expelled, thereby resulting in condensation on the cup and running the risk of the liquid coming into contact with the bulb.

In addition, a metal cup is difficult to handle after use because it is too hot.

Finally, persistent residual traces of the diffused perfume are to be found on the cup and may give rise to hazardous conflicting mixtures with different perfumes that have previously been diffused.

The device of the invention presents a much larger contact area between air and the material constituting the pad than is available in a solid material such as a cup insofar as the air is throttled as it were so that temperature is better distributed and hot points are no longer observed which could otherwise give rise to condensation in the cup.

Further, if condensation does occur, the structure of the device retains the condensate which is then eliminated by evaporation due to the device heating.

In addition, this device is much easier to handle after utilization insofar as it cools down much more quickly than does a hot cup.

Finally, there is no odor accumulation, i.e. no accumulation of traces of perfume in the texture of the pad element, and successive pellets soaked in different perfumes may be fitted thereto in succession without observing any conflicting mixture of perfumes.

Advantageously, the pad element is crimped and provided with a protecting metal grid.

BRIEF DESCRIPTION OF THE DRAWING

Implementations of the invention are described by way of example with reference to the accompanying drawing, in which:

FIG. 1 shows a pad type element in accordance with the invention.

FIG. 2 shows a metal wire for holding the device supporting the article of the invention in the proximity of an electric lightbulb.

DETAILED DESCRIPTION

The support element used was a washer or pellet constituted by a 100% chlorofiber non-woven needled sheet bonded by 100% polyvinyl chloride resin reference 3 333-B sold by the Nordlys Corporation.

This material is not flammable and it becomes heat shrinkable from 60° C. to 80° C. when impregnated with a perfume solution. It is also very light (density 65 $kg/m^3$ to 75 $kg/m^3$) and has very remarkable absorption properties.

The washer is impregnated with a dilution of perfume substance in dipropylene gylcol, with the concentration by weight of the perfume substance varying, for example, over the range 5% to 75% depending on the nature and the origin of the perfume, and in particular since they are more powerful, perfumes of chemical origin are used at lower concentrations than are perfumes of vegetable origin. Natural perfumes are used at a concentration of 20% to 50%.

The proposed washers or pellets have a diameter of 40 mm and a thickness of 4 mm, for example. These washers may shrink down to a diameter of about 10 mm which represents a volume shrinkage ratio of about 10 to 1 which demonstrates the large diffusion effect that can be obtained using such materials.

The washer is impregnated by being soaked in the perfume solution. A 40 mm washer as described can soak up several grams (g) of solution.

Advantageously, the quantity of liquid in this type of washer does not exceed 1 g so as to ensure that the quantity of liquid made available by shrinking does not exceed the quantity of liquid which can be evaporated by the heat given off by an electric lightbulb. for example.

This washer may be placed in the proximity of a heat source (radiator, flame, electric lightbulb) and a perfume substance can thus be diffused in the atmosphere for a period of more than 6 hours, and it should be understood that the washer may be used intermittently, since it does not lose perfume when not in use.

All sorts of shapes and volumes can be envisaged for the support element. An interesting variant consists in perforating the above-described washer, thereby increasing the contact area between the washer and ambient air, and thus facilitating diffusion of the perfume substance absorbed in the washer.

Advantageously, the article of the invention is placed in the proximity of an electric lightbulb using an article support device comprising a buffer element constituted by a stainless steel knit as sold under the trademark Knitmesh (ref. 613A) which is compressed into the form of a disk having a diameter which is substantially greater than the diameter of the above-described chlorofiber pellet. A pad element suitable for properly retaining condensate can be constituted using wires having a diameter of about ¼ of a millimeter (mm), and it is compressed so as to set up a headloss of about 20% to 30% in a fluid as it goes through the pad element, with the total thickness of the element being about 3 mm to 5 mm.

Once it has been compressed, this metal knit may be crimped and provided with a metal grid in order to prevent the shrunken fibers of the pellet tangling in use with the texture of the pad element, since such tangling would make it difficult to remove a used pellet. If the knit is thoroughly compressed, then a grid is not necessary.

Using a stainless material means that it can be cleaned in water or by using any other cleaning fluid.

FIG. 1 shows an unfinished specimen of the pad type element constituted by a multitude of intertwined and tangled stainless metal wires 5 which are then compressed. The pad element as shown is not crimped as it would be in a finished presentation of the device of the invention, as shown in FIG. 2.

This device may be fixed to an electric lightbulb by means of a metal wire 1 which holds it in the vicinity of a lightbulb 2. The metal wire 1 is fixed to the bulb 2 by one of its ends being in the form of two spring loops 4a and 4b, with the bulb being inserted between the two loops of the spring.

The other end 3 of the wire is fixed to the pad element of FIG. 1 e.g. by shaping said other end into a loop into which the texture of the pad element is forced, or by crimping the loop around the pad element.

I claim:

1. A method of diffusing a volatile substance comprising the steps of: absorbing said substance in a support element of heat shrink material which includes other than woven chlorofibers, bonded by a polyvinyl chloride resin, and diffusing said substance into an atmosphere by causing said support element to shrink through exposure to heat.

2. A method according to claim 1, wherein said heat is supplied by an electric lightbulb.

3. A method of diffusing a volatile substance according to claim 1, wherein the volatile substance is perfume.

4. A consumable article for diffusing an active volatile substance into an ambient atmosphere, comprising a support element of heat shrink material, wherein said substance is absorbed in said element and the support element comprises other than woven chlorofibers, bonded by a polyvinyl chloride resin.

5. An article according to claim 4, wherein the volatile substance is perfume.

6. A consumable article for diffusing an active volatile substance into an ambient atmosphere, comprising a support element of heat shrink material, wherein said substance is absorbed in said element and said substance is dissolved in a solvent which is of low or zero volatility at temperatures below a shrinkage temperature of said support element impregnated with said substance.

7. A consumable article for diffusing an active volatile substance into an ambient atmosphere, comprising a support element of heat shrink material, wherein said substance is absorbed in said element and said substance is diluted in an oily solvent.

8. An article according to claim 7, wherein the solvent is dipropylene glycol.

9. An article according to claim 7, wherein the oily solvent is glycol.

10. In combination, a device for supporting a consumable article for diffusing an active volatile substance into an ambient atmosphere, the article comprising a support element of heat shrink material, made of other than woven chlorofibers, bonded by a polyvinyl chloride resin, wherein the volatile substance is absorbed in said element; and the device comprising a pad element including intermeshed wires of metal material, which are compressed in order to produce the pad element, wherein said pad element is constructed and arranged to receive and support said consumable article.

11. The combination according to claim 10, wherein said pad element is a compressed knit of stainless steel or other metal wire.

12. The combination according to claim 10, wherein the device includes means for fixing the device on an electric lightbulb, said means for fixing comprising a metal wire, one end of said wire being connected to the device and the other end of the wire constructed for connection to a lightbulb, said other end being in the form of a two-loop spring, wherein said two loops may be placed on either side of a lightbulb for connection thereto.

* * * * *